United States Patent [19]

Miron et al.

[11] Patent Number: 5,618,680
[45] Date of Patent: Apr. 8, 1997

[54] USE OF LIGANDS SPECIFIC TO MAJOR HISTOCOMPATIBILITY COMPLEX-CLASS I ANTIGENS FOR DIAGNOSING ENDOMETRIOSIS

[75] Inventors: Pierre Miron; Denis-Claude Roy; Marie-Hélène Lachapelle, all of Laval, Canada

[73] Assignee: Institut de Medecine de la Reproduction de Montreal, Quebec, Canada

[21] Appl. No.: 365,085

[22] Filed: Dec. 28, 1994

[51] Int. Cl.$^6$ .................. C12Q 1/68; G01N 33/50
[52] U.S. Cl. .................. 435/7.21; 435/6; 435/7.5; 435/7.9; 435/806; 435/960; 435/975
[58] Field of Search .................. 435/7.24, 6, 7.21, 435/7.5, 7.9, 806, 960, 975; 530/388.7

[56] References Cited

U.S. PATENT DOCUMENTS

| | | | |
|---|---|---|---|
| 4,444,744 | 4/1984 | Goldenberg | 424/1.1 |
| 4,666,845 | 5/1987 | Mattes et al. | 435/240 |
| 4,675,286 | 6/1987 | Calenoff | 435/7 |
| 5,059,524 | 10/1991 | McKenzie et al. | 435/7.24 |
| 5,256,543 | 10/1993 | Pouletty et al. | 435/7.94 |

FOREIGN PATENT DOCUMENTS

| | | |
|---|---|---|
| 2011704 | 9/1990 | Canada . |
| 0387027A3 | 9/1990 | European Pat. Off. . |
| 92/18535 | 10/1992 | WIPO . |

OTHER PUBLICATIONS

Ota, H., and S. Igarashi, "Expression of Major Histocompatibility Complex Class II Antigen In Endometriotic Tissue In Patients With Endometriosis and Adenomyosis," *Fertility and Sterility*, pp. 834–838 (1993).

Oosterlynck et al., "Immunohistochemical Characterization of Leucocyete Subpopulations in Endometriotic Lesions", *Arch. Gynecol. Obstet.* 253:197–206 (1993).

Gleicher, N. et al. (1987). Obstetrics & Gynecology. 70(1): 115–122.

Johnson, P.M. et al. (1984). The Journal of Immunology. 132(4): 1608–1610.

Sakaguchi, S. et al. (1985). J. Exp. Med. 161: 72–87.

Satyaswaroop, P. G. (1979). Journal of Clinical Endocrinology and Metabolism. 48(4): 639–641.

I. Doxiadis et al, Vox Sang, 56, 196–199, 1989.

M. Kawata et al, Jour. Exper. Med., 160, 633–651, 1984.

*Primary Examiner*—David Saunders
*Attorney, Agent, or Firm*—Merchant, Gould Smith, Edell, Welter & Schmidt, P.A.

[57] ABSTRACT

It is an object of the present invention to provide the clinicians with a new application for ligands specific to MHC-class I antigens, especially HLA-ABC antigens, this new application residing in the detection and diagnosis of endometriosis. It is also an object of the present invention to provide a method and a test kit for diagnosing endometriosis, preferably by immunohistochemistry, using a monoclonal anti-HLA-ABC antibody as a preferred ligand or diagnostic reagent. This new method is non-invasive and is more reliable as a screening test than the conventionnally used laparoscopy. When the endometrium of a woman tests negatively with the claimed method, it prevents the use of laparoscopy which is an invasive method for detecting endometriosis. This method can be practiced on a specimen obtained from the endometrium of a patient and does not require a specimen sampled directly from the endometriotic foci.

13 Claims, 1 Drawing Sheet

USE OF LIGANDS SPECIFIC TO MAJOR HISTOCOMPATIBILITY COMPLEX-CLASS I ANTIGENS FOR DIAGNOSING ENDOMETRIOSIS

BACKGROUND OF THE INVENTION a) Field of the Invention

This invention relates to the use of ligands specific to a Major Histocompatibility Complex (MHC)-class I antigen, especially an HLA-ABC surface antigen, which is normally exposed at the surface of cell membranes, and which is therefore present in or on endometrial cell, for the diagnosis of endometriosis. The detection of this antigen is carried out according to a process comprising the reaction of a ligand, preferably an antibody, which is normally used to detect the presence of a MHC-class I antigen at the surface of all cells expressing it.

This invention also relates to a method for the diagnosis of endometriosis using the same ligand(s).

b) Description of Prior Art

Endometriosis is one of the most common disorders encountered in the field of gynaecology, affecting the health of an estimated 10 to 15% of women during their reproductive years. Although not life threatening, endometriosis is often associated with severe pelvic pain and infertility.

Endometriosis is classically defined as the presence of endometrial tissue (i.e. glands and stroma) outside the uterine cavity which is its normal location. Although various hypothesis have been proposed for its pathogenesis (i.e. transplantation, lymphatic and vascular metastasis, or coelomic metaplasia), there are several lines of evidence to support the idea that retrograde menstruation and implantation are the primary mode of developing pelvic endometriosis.

The implantation theory proposes that viable endometrial tissue is refluxed through the fallopian tubes and implants on the peritoneal surface or pelvic organs. Some additional etiologic factors must be present for the development of endometriosis and could be implicated in an altered immune function.

To date, there are no sensitive reliable, non-invasive methods for the diagnosis of endometriosis.

Over the last decade, an increasing number of reports suggest that endometriosis is associated with abnormal immune function. It was first suggested, in 1980, that changes in humoral immunity cause endometriosis. The C3 components of the complement and IgG antibodies have been found in the endometrium of women with endometriosis, with a reduction in the levels of total complement. In addition, IgG and IgA antibodies have been already identified in the ovarian and endometrial tissue of women with endometriosis.

Recently, a high incidence of autoantibodies to phospholipids (particularly phosphatidylserine) and to histones and nucleotides has also been reported (Gleicher, 1987), suggesting polyclonal B-cell activation in endometriosis. The presence of more generalized autoantibodies have suggested that endometriosis could be an autoimmune disease. The evidence for autoimmune involvement is, however, far from unequivocal and many important questions remain.

The possibility that cell-mediated immunity is altered in women with endometriosis was first suggested in 1980. The concentration and total number of peritoneal macrophages are increased in endometriosis as well as their activator status. The contribution of reactive oxygen metabolites (superoxide anion ($O_2^-$) hydrogen peroxide ($H_2O_2$) and singlet oxygen ($^1O_2$)) to the damage of adjacent normal tissues in the presence of endometriosis has been suggested by an increased chemiluminescence of peritoneal macrophages.

More recently, a defect in natural killer cell (NK) activity has been reported. This reduced activity of the NK cells could also be present locally, at the level of the peritoneal fluid. Moreover, women with endometriosis show significantly more T-cell suppressor/cytotoxic in their peritoneal fluid.

Even though a defect in the activity of the NK cells has been noted in the presence of endometriosis, an increased resistance of the endometrial cells to the NK mediated cytotoxicity was also suggested. The mechanisms involved in this endometrial resistance have remained unexplained.

In the last five years, a considerable amount of research has been directed towards the development of a better diagnostic method for endometriosis. However, a problem lies in the fact that women suffering from endometriosis may not exhibit any symptoms other than infertility or they may only exhibit symptoms that mimic those of many other gynaecological diseases.

Hitherto, it has been common to use an invasive surgical method requiring general anesthesia to diagnose endometriosis, such as laparoscopy or laparotomy which allows the direct visualization of the pelvic content. However, there are certain disadvantages in using this difficult and inaccurate method for diagnosing endometriosis.

One such disadvantage of this method is that it is sometimes difficult to detect cases of minimal endometriosis. In addition, other disadvantages exist resulting from, for example, the presence of adhesions which can obscure the direct visualization of the pelvis, making it impossible to even carry out a laparoscopy; or from the presence of ovarian endometriomas which are often similar in appearance to functional ovarian cysts and could result in these endometriomas being misdiagnosed. Moreover, up to sixteen descriptive types of endometriosis have been identified recently, which can make the diagnosis of endometriosis even more difficult. Furthermore, what is even more worrisome is the fact that certain microscopic foci of endometriosis, which are not identifiable by laparoscopy, have been identified and documented using a peritoneal biopsy by scanning with an electron microscope.

Therefore, even with an increased use of laparoscopy, endometriosis remains a frequently underdiagnosed condition.

In general, imaging techniques such as ultrasonography, CT scanning, and magnetic resonance imaging (MRI) have limited value in the diagnosis of endometriosis. They can provide information about the invasiveness of the disease, but none of these imaging techniques are able to identify superficial diseases of peritoneal surfaces. Moreover, the high cost of these procedures rarely justifies their use for the diagnosis of endometriosis.

The technique of using antibodies like, for instance, anti-endometrial antibodies as mentioned hereinabove in a method for the diagnosis of various diseases is a widespread and well known technique.

In U.S. Pat. No. 4,444,744, an improved method is provided for using radiolabelled antibodies to detect the presence of cell surface antigens, including the type HLA-A, HLA-B AND HLA-DR surface antigens located on cancer cells, in order to locate and diagnose these cancer cells.

These highly specific radiolabelled antibodies against the cell surface antigens are also used in a method for tumour therapy.

In U.S. Pat. No. 4,666,845, labelled mouse monoclonal antibodies, namely MF116, MH94, MD144, MH55, MF61, ME46, and ME195 were used to detect the presence of a plurality of surface antigen on human endometrial, cervical or uterine cancer cells and to diagnose these cancer cells.

These labelled monoclonal antibodies are also used in the treatment of endometrial, cervical or uterine cancers.

In Canadian patent publication number 2,081,900, a method of diagnosing endometriosis is described. This method detects the presence of particular antibodies which are present in specimens obtained from patients suffering of endometriosis. The antigens used as an immunogical reagent were isolated from the cytoplasm of epithelial adenocarcinoma cells. These antigens have been characterized only by their molecular weight and by their ability to bind the antibodies to be detected.

In Canadian patent publication number 2,011,704, two methods of diagnosing endometriosis are described. One makes use of an antibody, particularly the MS2B6 monoclonal antibody, to detect endometrial antigens, while the other makes use of antigens also isolated from epithelial carcinoma cells to detect the presence of anti- endometrial antibodies. No attempt is made in this application to clarify the similarity or the complete identity of the antigens of both methods neither to clarify the similarity or equivalence of the MS2B6 antibody with regard to the endometrial antibodies. Furthermore, the antigens isolated from carcinoma cells are also grossly characterized by their molecular weight and their ability to bind the antibodies to be detected.

The first two patents are directed to the use of monoclonal antibodies to detect surface antigens present on various cancer cells, including endometrial cancer cells, and to the diagnosis of these cancer cells. In all cases, the expression of surface antigens of cancer cells cannot be considered as being similar to surface antigens found on endometrial cells of a woman suffering from endometriosis.

Therefore, the particular techniques illustrated in these patent documents could not be used as a method for diagnosing endometriosis or for detecting the different expression of surface antigens on endometrial cells of a woman with endometriosis.

In light of these results, there is clearly a great need for a non-invasive diagnostic test which is more reliable than the previous techniques and which is easier for both the patient and the physician. This new test may decrease the need for laparoscopy in women with pelvic pain or infertility.

SUMMARY OF THE INVENTION

The Applicant has found surprisingly that a woman with endometriosis has a different expression of the Major Histocompatibility Complex (MHC) class I antigens (especially HLA-ABC surface antigens) in or on their endometrial cells, when compared with the expression of the same antigens of endometrial cells of a healthy woman. Possibly, this difference in the expression of the MHC class I antigens prevents their recognition and cytolysis by the NK (natural killer) cells. This therefore may explain why the endometrial cells found in the peritoneal cavity are not destroyed, following retrograde menstruation and their subsequent peritoneal implantation. The presence of a different expression of these antigens on endometrial cells is therefore predictive of endometriosis.

A large number of ligands, particularly monoclonal antibodies, that bind the aforesaid antigens normally expressed on the surface of a large number of human cells are available. Some authors (Johnson et al., 1984 and Sakaguchi et al., 1985) have evaluated the antigenic expression of the HLA-ABC antigens on the surface of endometrial cells. However the expression of the HLA-ABC antigens has never been correlated with the presence or absence of endometriosis. This is the first proposal suggesting that endometrial cells from patients with endometriosis express MHC-class I antigens, especially the HLA-ABC antigens, differently from normal individuals or other patients.

Therefore, it is an object of the present invention to provide the clinicians with a new application for ligands specific to MHC-class I antigens, especially HLA-ABC antigens, this new application residing in the detection and diagnosis of endometriosis.

It is also an object of the present invention to provide a test for diagnosing endometriosis, especially a non-invasive and reliable screening test, using a ligand to these antigens for the diagnosis of endometriosis. This antigen is present in or on endometrial cells or cells having the same embryonic origin (especially endocervical cells). Therefore, this method can be praticed on a specimen obtained from the endometrium of a patient and does not require a specimen sampled directly from the endometriotic foci. The detection of these antigens carried out according to a process comprising the reaction of a ligand, e.g. antibodies with the antigens normally expressed at the surface of endometrial cells.

According to a preferred embodiment of the invention, the test uses a ligand to an antigen originating from endometrial cells. The MHC-class I antigens to which it will be referred hereinbelow are defined as comprising HLA-ABC antigens and related molecules. Such related molecules include proteic precursors like immature proteins, portions of these antigens as well as messenger RNAs and cDNAs. When proteins are targetted, the ligand of choice is an antibody specific thereto, and when messenger RNAs encoding these proteins are targetted, nucleotidic probes hybridizable thereto might be used to detect the difference of expression of these antigens.

MHC class I antigens, especially HLA-A, B and C antigens, are human cell surface glycoproteins. It is generally assumed that the Major human Histocompatibility Complex class I antigens, are expressed by nucleated cells with some exceptions like thymus, kidney or thyroid cells. They have a role in the interaction between cytotoxic T-cells and target cells.

BRIEF DESCRIPTION OF THE FIGURES

The invention will be better understood upon reading the following non limitative description of preferred embodiments of it, reference being made to the accompanying figures in which.

DESCRIPTION OF PREFERRED EMBODIMENTS OF THE INVENTION

Figure 1:
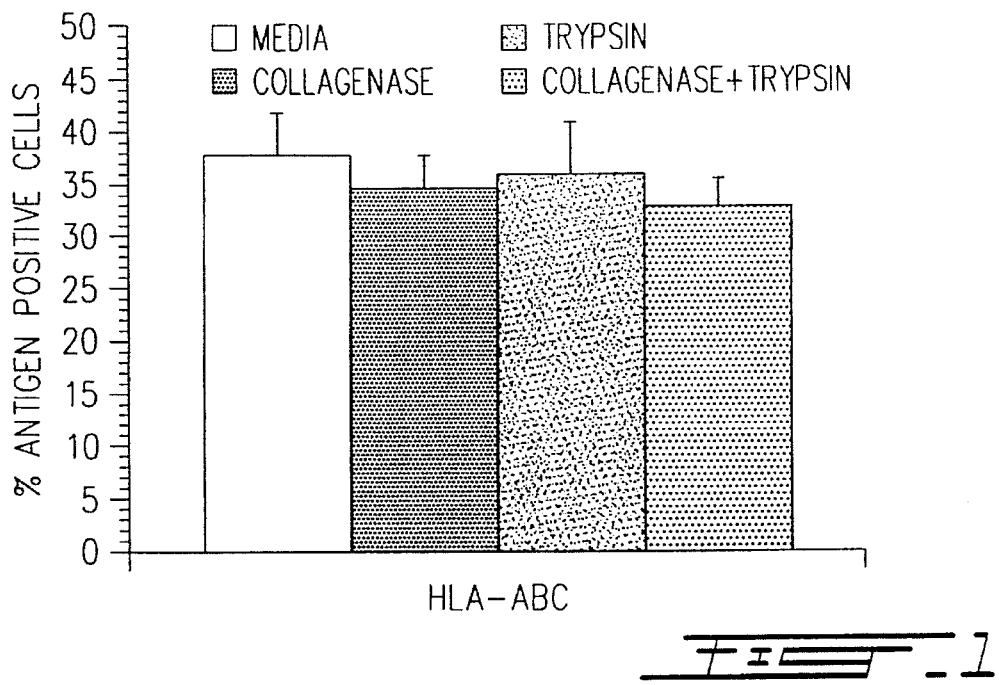
FIG. 1: Effect of collagenase and trypsin on the detection of HLA-ABC surface antigens. Peripheral blood lymphocytes (PBL) were incubated with media and collagenase 0.25% for 2 hours at 37° C., or trypsin 0.1% for 12 minutes at 37° C. The cells were labelled with a monoclonal antibody directed against HLA-ABC surface antigens and analyzed by flow cytometry (n=3)

The ligands usable in the present invention are available from different sources. Examples of ligands include antibodies directed to MHC-class I antigens, especially antibodies directed to HLA-ABC antigens, nucleotidic sequences, especially cDNA molecules or oligonucleotides which are complementary to mRNAs or to cDNAs encoding these antigens, and receptors to these antigens. Among these ligands, the monoclonal antibody produced by the hybridoma PHM4 has been found particularly suitable to detect the presence of endometriosis. This monoclonal antibody is commerciallized by Chemicon (Temecula, Calif.) as a ligand for the identification of HLA-ABC cells. The binding of these ligands to the targetted antigens is monitored by labelling means. These labelling means comprise but are not limited to markers selected from the group consisting of radioisotopes, fluorochromes, enzymes, biotin and electron dense molecules.

The radioisotopes used for labelling may be selected from the group consisting of $^{125}I$, $^{131}I$, $^{32}P$, $^{3}H$, thallium, technetium, strontium, indium and yttrium. The enzymes used for labelling may be selected from the group consisting of peroxidase, esterase and alkaline phosphatase.

The electron dense molecules used for labelling may be selected from the group consisting of ferritin, gold and latex spheres.

The endometrial cells or cell components thereof may be evaluated on tissue section or may be suspended in an excipient (for example RPMI-1640 medium, Roswell Park Memorial Institute) to define a suspension. This cell suspension may be obtained by a process comprising a mechanical disruption and/or enzymatic treatment of endometrial tissue. The cells are mounted and fixed on a support suitable for analysis purposes.

The step of the method mentioned hereinabove, where the labelled antibody is being detected, may be carried out according to a procedure comprising the step of counter-staining the cells to reveal the presence of the endometrial cells or endometrial cell components and detecting a resulting coloration of the antigen with appropriate detection means.

These detection means may be selected from the group consisting of enzyme-linked immunosorbent assay, solid phase radiobinding immunoassays where the antibodies may be directed either against soluble antigens or cell surface antigens, autoradiography, competitive binding radioimmunoassay, immunoradiometric assay (IRMA), electron microscopy, peroxidase anti-peroxidase (PAP) labelling, fluorescent microscopy, alkaline phosphatase labelling, peroxydase labelling, an apparatus or material for measuring radioactivity, electrophoresis, Western blotting, Northern blotting, Southern cDNA blotting, flow cytometry, optical microscopy, spectrophotometry, a densitometer, an apparatus for measuring light reactivity, an apparatus for colorimetric determination and a polymerase chain reaction (PCR).

In the case where the detection means used is optical microscopy, the cells are mounted and fixed on a microscope slide. In this case, the step of detecting the labelled antibody is carried out according to a procedure comprising the step of counter-staining the cells to reveal the presence of the endometrial cells or endometrial cell components, and detecting a resulting coloration of the antigen with an optical microscope.

When the cells are mounted on a microscope slide, they may be mounted by cytocentrifugation or other mounting techniques known in the art (e.g. smearing).

When the endometrial tissue comprising endometrial cells is fixed on a microscope slide, it may be fixed according to a technique selected from the group consisting of cryosection and paraffin-embedding.

However, the cells or cell components can also be suspended in an excipient to define a suspension and/or simply smeared on a microscope slide for direct cytological analysis.

In the case where the cells are analyzed in order to detect the antigens by either enzyme-linked immunosorbent assay, solid phase radiobinding immunoassays where the antibodies may be directed either against soluble antigens or cell surface antigens, autoradiography, competitive binding radioimmunoassay, immunoradiometric assay (IRMA), electron microscopy, peroxydase anti-peroxidase tPAP) labelling, fluorescent microscopy, alkaline phosphatase labelling, peroxidase labelling, an apparatus or material for measuring radioactivity, electrophoresis, Western blotting, Northern blotting, Southern cDNA blotting, flow cytometry, optical microscopy, spectrophotometry, a densitometer, an apparatus for measuring light reactivity, an apparatus for colorimetric determination and a polymerase chain reaction (PCR), the endometrial cells or cell components may be suspended in an excipient to define the suspension, isolated by a process comprising a mechanical disruption of endometrial tissue and the suspension is then digested.

In the case where electrophoresis is used for protein detection, the endometrial cells or cell components may be suspended in an excipient to define a suspension and may be obtained by a process comprising a mechanical disruption of endometrial tissue. Advantageously, the suspension is then digested and deposited in a well of an electrophoresis gel. Next, the antigen is migrated through said gel by electrophoresis so that the antigen is isolated. Then the migrated antigens are transferred onto a membrane (e.g. nitrocellulose, nylon). Next, either a labelled antibody is reacted with the aforesaid membrane, or an antibody is reacted with aforesaid membrane and reacted with the antigen, and then a labelled antibody is further added to aforesaid membrane, and reacted with the antibody having already reacted with the antigen. The labelled antibody is then detected by detection means.

The detection means mentioned hereinabove may be selected from the group consisting of an apparatus for colorimetric determination, an apparatus for measuring light reactivity and an apparatus for measuring radioactivity.

Advantageously, the cells evaluated may be obtained from the endometrium.

The endometrial cells or cell components should be glandular endometrial cells or cell components.

EXAMPLE 1

Advantageously, as a particularly preferred direct method of detection of HLA-ABC surface antigens of endometrial cells for the diagnosis of endometriosis, the following steps may be carried out:

Step 1
Cell preparation
1.1 Endometrial biopsy with Wallach™ endocell (Pharmascience) or any other endometrial sampler
1.2 Mechanical disruption of endometrial tissue and filtration through a 250 μm stainless steel sieve
1.3 Collect by backwash endometrial glands retained on the filter
1.4 Dissociate glands by incubation with trypsin 0.25% for 10 minutes at 37° C. and wash 2× with RPMI supplemented with 2.5% human AB (HAB) serum (Gibco, Grand Island, N.Y.)

Step 2
Evaluation of % of cells expressing HLA-ABC
2.1 Approximately $5 \times 10^5$ cells obtained after step 1.4 are incubated with monoclonal antibodies including an anti-HLA-ABC antibody (Chemicon) and a negative isotype control antibody (Coulter, Hialeah, FA) for 30 minutes at 4° C.
2.2 Wash cells twice with 2.5% HAB serum in RPMI
2.3 Incubate with Goat anti-Mouse Ig conjugated to FITC (Coulter) for 30 minutes at 4° C.
2.4 Wash cells twice with 2.5% HAB serum in RPMI
2.5 Fix in 0.1% formaldehyde
2.6 Determine immunofluorescence reactivity by flow cytometry to determine the percentage of cells expressing HLA-ABC Step 3
Alternative to enhance specificity of detection of HLA-ABC antigens
3. In order to confirm that HLA-ABC expression is evaluated specifically on glandular cells, it is possible to identify glandular cells by monoclonal antibody labelling. Instead of step 2, the endometrial cells are first permeabilized and then labelled with an anti-cytokeratin monoclonal antibody conjugated with FITC (Becton-Dickinson, San Jose, Calif.). HLA-ABC expression is evaluated only on cells gated for cytokeratin positivity. We have previously shown that cell permeabilization does not impair detection of HLA-ABC expression (FIG. 1)
3.1 Endometrial cells obtained from step 1.4 are spun down and supernatant removed
3.2 Cells are put on ice and cold ethanol (−80° C.) is slowly dripped on the cells
3.3 This cell mixture is incubated at 4° C. for 30 minutes
3.4 Cells are washed twice with 2.5% HAB serum in RPMI 1640 and divided into four tubes (approximately $5 \times 10^5$ cells per tube)
3.5 Following antibodies are added to the different tubes:
  tube 1: negative MsIg (source; same isotype as anti-HLA) unconjugated antibody
  tube 2: keep at 4° C. until step 3.7
  tube 3: anti-HLA unconjugated antibody
  tube 4: keep at 4° C. until step 3.7
3.6 Mixture is incubated at 4° C. for 30 minutes and then tubes 1 and 3 are washed twice with 2.5% HAB serum in RPMI
3.7 Following reagents are added to the different tubes and incubated at 4° C. for 30 minutes:
  tube 1: Goat anti-Mouse Ig conjugated to FITC
  tube 2: negative Goat anti-MsIg (Coulter) conjugated to FITC
  tube 3: Goat anti-Mouse Ig conjugated to FITC
  tube 4: anti-cytokeratin antibody conjugated to FITC
3.8 Cells are washed twice with 2.5% HAB serum in RPMI and fixed in 0.1% formaldehyde
3.9 Flow-cytometry is used to determine the percentage of cells expressing cytokeratin using standard techniques known in the art
3.9.1 Gating is then performed on cytokeratin positive cells and further evaluation is done only on these gated cells
3.9.2 Cytokeratin positive cells gated are evaluated: Expression of HLA-ABC is then evaluated using cells from tube 4 and negatively labelled cells from tube 2 are used as negative controls
3.9.3 This assay allows determination of the percentage of endometrial cells expressing HLA-ABC

EXAMPLE 2

Also, as another particularly preferred method of detection of HLA-ABC surface antigens of endometrial cells for the diagnosis of endometriosis, the following steps may be carried out:

Step 1
Cell preparation
1.1 Endometrial biopsy with Wallach™ endocell (Pharmascience) or any other endometrial sampler
1.2 Tissue section by cryosection and then mounted on slide Step 2
Evaluation of % of cells expressing HLA-ABC
2.1 Proceed to fixation with acetone/methanol (3:1) for 6 minutes
2.2 Wash with Tris-HCL buffer for 5 minutes
2.3 Incubation with blocking agent (BSA 0.5%) for 5 minutes
2.4 Add anti-HLA-ABC antibody and incubate for 30 minutes
2.5 Wash with Tris-HCL buffer 3× for 1 minute
2.6 Incubate with second antibody biotinylated (Dako, Pittsburg, Pa.) for 10 minutes
2.7 Wash with Tris-HCL buffer 3× for 1 minute
2.8 Incubate with enzyme-conjugated streptavidin for 10 minutes
2.9 Wash with Tris-HCL buffer 3× for 1 minute
2.10 Incubate with substrate for 10 minutes
2.11 Wash 1× with tap water for 1 minute
2.12 Counter-stain with Mayer's heamalun for 1 minute
2.13 Wash in tap water for 5 minutes
2.14 Mount slide with aqueous solution and read under optical microscope to determine the percentage of cells expressing HLA-ABC

EXAMPLE 3

Furthermore, as still another particularly preferred method of detection of MHC Class I surface antigens in endometrial cells by electrophoresis for the diagnosis of endometriosis, the following steps may be carried out:

Step 1
Cell preparation
1.1 Endometrial biopsy with Wallach™ endocell (Pharmascience) or any other endometrial sampler 1.2 Mechanical disruption of endometrial tissue and filtration through a 250 μM stainless steel sieve 1.3 Collect by backwash endometrial glands retained on the filter 1.4 Dissociation of glands by incubation with trypsin 0.25% for 10 minutes at 37° C. and wash 2× with RPMI supplemented with 2.5% FCS Step 2

Gel technique 2.1 Preparation of 1% SDS—12% polyacrylamide gel 2.2 Mix cell suspension with equal volume of loading buffer 2.3 Place the sample in boiling-water for 10 minutes 2.4 Deposit mixed suspension in wells and run in conventional manner the electrophoresis gel 2.5 When the SDS-polyacrylamide gel is approaching the end of its run, rinse the graphite plate with distilled water and wipe off any beads of liquid that adhere to them with Kimwipes™

2.6 Cut six pieces of Whatman™ 3MM paper and one piece of nitrocellulose filter (Millipore) to exact size of the SDS-polyacrylamide gel 2.7 Float the nitrocellulose filter on the surface of a tray of deionized water and allow it to wet from beneath by capillary action. Then submerge the filter in the water for at least 5 minutes 2.8 Soak the six pieces of Whatman™ 3MM paper in a shallow tray containing a small amount of transfer buffer 2.9 Set up the transfer apparatus 2.10 Place the upper electrode on top of the stack, graphite side down. Connect the electrical leads and apply a current of 0.65 mA/sq. cm of gel for a period of 1.5–2.0 hours 2.11 Disassemble the transfer apparatus from the top downward, peeling off each layer in turn. Transfer the gel to a tray containing Coomassie Brillant Blue and stain it 2.12 Cut off the bottom left-hand corner of the filter and stain the filter with a radiolabelled antibody or other suitable probe against HLA-ABC surface antigens and visualize by autoradiography to detect said surface antigens The examples which follow provide an illustration of the characteristics and advantages of the present invention, without however limiting its scope.

EXAMPLE 4

METHOD OF OBTAINING ENDOMETRIAL TISSUE SAMPLES

The endometrial tissue samples were obtained from 60 women undergoing diagnostic laparoscopy, from infertile patients attending a fertility clinic, from women undergoing procedures related to gynaecological pathologies or from women undergoing tubal ligation. These samples were taken with a Wallach™ endocell sampler (Pharmascience, Montréal, Québec), during the secretory phase of the menstrual cycle (between the 18th day and the 25th day of the cycle). The samples were placed into sterile RPMI-1640 (Roswell Park Memorial Institute) medium (Gibco, Grand Island, N.Y.) and supplemented with 10% heat-inactivated Fetal Calf Serum (Gibco, Grand Island, N.Y.), 2% L-glutamine and 1% penicillin/streptomycin. Of course, the samples may have been placed in other culture media or aqueous suspensions suitable to maintain cell viability.

ISOLATION OF A GLANDULAR ENDOMETRIAL CELL

The endometrial tissue was suspended in an excipient (RPMI-1640) and mechanically disrupted using Pyrex™ glass Broeck™ tissue grinders (Fisher, Nepean, Ont.) in order to obtain an endometrial cell or cell component suspension. The alternative excipient may be selected amongst well known media.

The suspension was then filtered through a 250 μM stainless steel sieve (Millipore, Marlborough, Mass.), where the glands were retained on the filter, while the stromal enriched fraction passed through the filter. These glands were recovered from the filter by backwashing with RPMI medium.

The glandular cells or cell components were then incubated with collagenase type I 0.25% (Sigma, St-Louis, Mo.) for about 2 hours at 37° C., in a shaking waterbath. Subsequently, the glandular cells or cell components were incubated with trypsin 0.1% (Sigma, St-Louis, Mo.) for about twelve minutes at 37° C. The enzymatic reaction was stopped with 500 μL of normal human serum. After treatment with trypsin 0.1%, the glandular endometrial cell was washed twice with RPMI medium.

Another method (Satyaswaroop, 1979) may be used to isolate a glandular endometrial cell. Here, the endometrial tissue is cut into about 1 mm. pieces and treated with 0.25% collagenase at 37° C., in a shaking water bath for two hours. This collagenase-treated tissue is then strained through a 250 μM sieve in order to retain the undigested tissue and mucous material. The filtrate is then passed through a 38 μM or 105 μM sieve in order to retain the glands. In order to disperse the glands into single glandular epithelial cells, it is possible to add a second incubation period. The glands were then resuspended in 3 mL of trypsin 0.025%-EDTA 0.01% and in PBS/BSA, and then incubated for seven to twelve minutes. However, there are disadvantages with this technique in that firstly, one must carry out additional filtrations on 38 μM or 105 μM sieves to obtain these glands and secondly, because the purity after the second filtration would not be as good as that for the initial method.

The endometrial tissue can also be evaluated on a slide without being in suspension, using the techniques of cryosection or paraffin-embedding of tissues.

CYTOCENTRIFUGATION

The endometrial cells were taken at different steps of the isolation procedure or sorted using flow cytometry, evaluated for viability and then cytocentrifuged (Shandon Cytospin II, Pittsburgh, Pa.) and dried on a slide for thirty minutes. The slide was then stained with Papanicolaou stain (Sigma, St-Louis, Mo.) for morphological confirmation, or with various monoclonal antibodies.

With regard to the evaluation for viability, it is to be noted that the glandular cells were well dispersed and conserved their integrity. In order to evaluate the purity of the glandular fraction, the glandular cells were measured with a monoclonal antibody (mAB) directed against the cytokeratin 14–18 antibody and visualized by alkaline phosphatase staining. The glandular fraction was contaminated by less than 25% of cells which were negative for the presence of cytokeratin 14–18 (Table I).

TABLE I

|  | DETECTION ON CYTOCENTRIFUGED CELLS | DETECTION BY FLOW CYTOMETRY |
| --- | --- | --- |
| % PURITY | 75 | 96 |
| % HLA-ABC WITHOUT ENDOMETRIOSIS | 31 ± 24 | 22 ± 11 |
| % HLA-ABC WITH ENDOMETRIOSIS | 90 ± 10 | 79 ± 11 |

The contamination was made by the presence of the stromal cells (i.e. fibroblast-derived cells and leucocytes). Other isolation techniques can also be used which give similar results.

The cytocentrifuged cells were fixed on the microscope slide with a mixture of acetone/methanol (3:1) for ten (10) minutes and washed 2 times with Tris-HCl buffer for five minutes. Optionally, the cells may be washed 2 or 3 times with Tris-HCl buffer for 1 to 5 minutes. The cells can be fixed using other well known fixation techniques known in the art.

A blocking reagent, BSA 0.1%, was then added for five minutes to saturate non-specific binding sites. Powdered milk may also be used as a blocking reagent. Optionally, the blocking reagent, BSA 0.1%, may be added for five to thirty minutes.

ADDITION OF A MONOCLONAL ANTIBODY BY INDIRECT IMMUNOHISTOCHEMISTRY

The slide was incubated with a primary mouse monoclonal antibody for thirty minutes at room temperature and washed three times with Tris-HCl buffer for five minutes each time. The antibody selected was an anti-HLA-ABC (Chemicon, Temecula, Calif.). The slide was reincubated with an anti-mouse Immunoglobulin-biotinilated monoclonal antibody for 10 minutes at room temperature, and washed three times with Tris-HCl buffer for five minutes each time. Optionally, the incubation times for both monoclonal antibodies may vary from 30 minutes to 1 hour at a temperature varying from 4° C. to room temperature.

Optionally, the slide may be washed between each exposure to antibody, 2 or 3 times with Tris-HCl buffer for 10 1 to 5 minutes.

Streptavidine conjugated with alkaline phosphatase was then added to form a complex with biotin already associated with the anti-mouse Immunoglobulin monoclonal antibody, for ten minutes and the slide was again washed three times with Tris-HCl buffer for five minutes each time. Optionally, the slide may be washed 2 or 3 times with Tris-HCl buffer for 1 to 5 minutes. The slide was developed with the addition of a chromogenic substrate for ten minutes, and washed with tap water for one minute. The cytospin slide was counterstained with Mayer's haemalun (BDH, Toronto, Ont.) for one minute and washed with tap water for another five minutes. Other stains known in the art like Wright-Giemsa may be used to counterstain the slides. Finally, the slide was mounted with Immu-mount (Shandon, Pittsburgh, Pa.). The staining was evaluated by optical microscopy in at least 3 times 100 cells. When the endometrial cells express the HLA-ABC surface antigen, these cells have their surface antigens revealed by a characteristic coloration.

Figure 2:
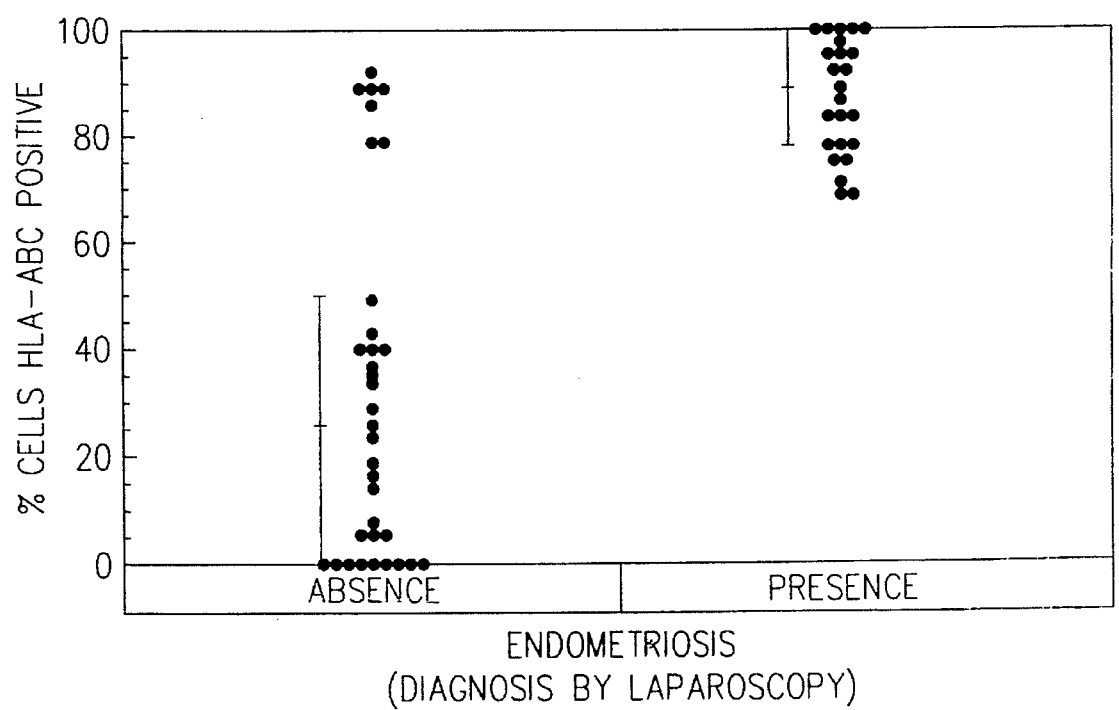
FIG. 2: Expression of the MHC class I surface antigens on glandular endometrial cells versus the results obtained with laparoscopy. The cytocentrifuged endometrial cells of women were analyzed by indirect immunohistochemistry to determine the percentage of cells expressing HLA-ABC antigens. These results were compared with the results obtained by performing a laparoscopy on these same women (n=60).

FIG. 2 shows the expression of HLA-ABC antigens at the surface of glandular endometrial cells of women suffering or not of endometriosis versus the diagnosis obtained by performing laparoscopies on these women. The laparoscopy results showed that for 60 women tested, 35 did not have endometriosis while 25 did have endometriosis. However, using our indirect immunohistochemical method, 7 of the 35 women who did not have endometriosis by laparoscopy, showed a high percentage (specificity>80%) of endometrial cells expressing HLA-ABC antigens with a different expression, which is predictive of endometriosis. Therefore, the results obtained by laparoscopy suggest that they could be less reliable than those with our indirect immunohistochemical method which showed a 100% sensitivity. For example, it has been demonstrated that false negative results with laparoscopy could occur in women with microscopic endometriosis. In our indirect immunohistochemical method, women without endometriosis expressed only 31±24% (mean±S.D.) while women with endometriosis expressed 90±10% HLA-ABC antigens. Class II Major Histocompatibility Complex antigens were not expressed at the surface of glandular endometrial cells from women with or without endometriosis (data not shown). It should be deduced from the results shown in FIG. 2 that all women with laparoscopically diagnosed endometriosis have at least about 65% of their endometrial cells expressing HLA-ABC antigens. In the presence of negative results (less than 65%) in our immunohistochemical diagnostic test, endometriosis would be ruled out, preventing the need for a laparoscopy in these women. However, in the presence of positive results (≧65%) in our immunohistochemical diagnostic test, laparoscopy could still be necessary in these womem to evaluate the invasiveness (stage 0 to IV) of endometriosis.

It was further verified that enzymatic steps in the isolation method mentioned hereinabove, do not cleave the epitope of antigenic structures found on a cell surface. In order to verify this, normal peripheral blood mononuclear cells were treated with collagenase and trypsin, as they are used for this isolation procedure, in order to evaluate whether or not enzymatic treatment has an effect on the expression of surface antigens of peripheral blood lymphocytes (PBL) from normal donors.

Indeed, antigenic structures could be cleaved by enzymatic treatment resulting in a modification of the pattern of expression of different surface antigens, for example leading to the absence of detection of an antigen that is really present on native cells but cleaved by the enzymatic treatment.

PBL were incubated with collagenase type I 0.25% (Sigma, St-Louis, Mo.) for 2 hours at 37° C. in a shaking waterbath and washed twice and with trypsin 0.1% (Sigma, St-Louis, Mo.) for 12 minutes at 37° C. Enzymatic reaction was stopped with 500 μL of normal human serum. As control, PBL were incubated with medium only (no enzymatic treatment). Treated and untreated cells were then labelled with monoclonal antibodies for immunofluorescence analysis.

As shown in FIG. 1, treatment with collagenase or with trypsin did not affect the recognition of HLA-ABC surface antigens on PBL. Although this immunological evaluation was performed on peripheral blood cells, it is possible to extrapolate that the enzymatic treatment will not affect recognition of HLA-ABC surface antigens on glandular endometrial cells.

EXAMPLE 5

FLOW CYTOMETRY

All the procedures set forth in step 1 of Example 1 were repeated until the addition of the monoclonal antibody. This addition is then carried out according to the following steps:

A panel of monoclonal antibodies was used. The cytokeratin conjugated antibody with FITC (Becton Dickinson, San Jose, Calif.) and an unconjugated HLA-ABC were used. Labelling of cells with this panel of monoclonal antibodies was performed using standard techniques known in the art.

Briefly 0.5 times $10^6$ cells were incubated with monoclonal antibodies for 30 minutes at 4° C., then washed twice. A second incubation was performed for the unconjugated antibody with anti-MsIg conjugated to phycoerythin (PE) for 30 minutes at 4° C., then washed twice and fixed in 0.1% formaldehyde. Immunofluorescence reactivity was determined by flow cytometry analyzing $10^4$ cells in each sample. Flow-cytometry (FACstar plus, Becton-Dickinson, San Jose, Calif.) was performed with an argon laser operating at 488 nm with an intensity of 200 mW. Background fluorescence was determined using isotype-matched nonreactive directly or indirectly conjugated monoclonal amibodies (MsIg-FITC and PE) and was <1% for all analyzed. Table I shows the results for 12 samples analyzed by flow cytometry. Women without endometriosis expressed only 22±11%, in contrast with women with endometriosis who expressed 79±11% HLA-ABC antigens.

DIAGNOSTIC KIT

The method of diagnosing endometriosis according to this invention can be practiced by way of a diagnostic kit. Such a kit should contain all the essential elements to perform one of the preferred methods, which choice depends on the laboratory facilities available to the practician. Such essential elements are the following for detecting the presence of antigens:

Indirect detection:

a first antibody consisting of an anti-MHC class I antibody, preferably a monoclonal anti-HLA-ABC antibody, and a labeled second antibody which binds antibodies all the antibodies of the first species.

Direct detection:

a labeled anti-MHC class I antibody, preferably a monoclonal anti-HLA-ABC antibody.

Optional reagents and material:

When the method involves disruption of the sample cells as in Example 1, reactants like trypsin, RPMI and human AB serum may optionnally enter the composition of the kit as well as any buffer or reagent for the revelation of the binding of the antibodies to the antigens and the disposable instruments and reagents for sampling endometrium. Optionally, a labeled appropriately selected anti-cytokeratin antibody.

When the method involves the mounting of a biopsy on a slide as in Example 2, the same optional components may enter the composition of the test kit except for the material and buffer for disrupting the cells.

When the method involves the separation of proteins by electrophoresis as in Example 3, no human AB serum is necessary. Also, the material and reagents necessary for the electrophoresis and subsequent blotting may be added.

What is claimed is:

1. A method for diagnosing endometriosis comprising: contacting a biological sample containing glandular endometrial cells with a ligand which specifically binds a Major Histocompatibility Complex (MHC)-class I antigen, a proteic precursor or a protein fragment thereof, or a messenger RNA or a cDNA to a messenger RNA encoding said antigen, precursor or fragment; wherein the ligand forms a complex with said antigen precursor or fragment, and the presence of the complex is an indication of the presence of endometriosis.

2. A method according to claim 1 wherein said MHC-class I antigen is a Human Leucocyte Antigen (HLA)-ABC surface antigen and said ligand is an anti-HLA-ABC antibody.

3. A method according to claim 2 wherein said anti-HLA-ABC antibody is produced by the hybridoma PHM4.

4. A method for diagnosing endometriosis which comprises:

reacting a first ligand which specifically binds a Major Histocompatibility Complex (MHC)-class I antigen, a proteic precursor or a proteic fragment thereof, with a biological sample containing glandular endometrial cells to form a complex, said complex being detected by labeling means, the label being present on said first ligand or the label being present on a second ligand which binds the first ligand or the label being present on a first reactive member of said labeling means, said first member reacting with a second reactive member present on said first or second ligand; and detecting the complex, wherein the presence of a percentage of labeled glandular endometrial cells greater than about 65% is an indication of the presence of endometriosis.

5. A method according to claim 4 wherein said glandular endometrial cells are isolated from said biological sample.

6. A method according to claim 4 wherein said glandular endometrial cells are identified and numbered by counterstaining.

7. A method according to claim 4 wherein said glandular endometrial cells are identified and numbered by means of their binding to an anti-cytokeratin antibody.

8. A method according to claim 4 wherein said MHC-class I antigen is a Human Leucocyte Antigen (HLA)-ABC surface antigen and said first ligand is an anti-HLA-ABC antibody.

9. A method according to claim 8 wherein said anti-HLA-ABC antibody is produced by the hybridoma PHM4.

10. A method according to claim 4 wherein said labelling means is selected from the group consisting of radioisotopes, fluorochromes, enzymes, biotin/avidin and electron dense molecules.

11. A test kit for diagnosing endometriosis comprising: a ligand which specifically binds a major Histocompatibility Complex (MHC)-class I antigen; an anti-cytokeratin antibody and labeling means for the ligand and the antibody.

12. A test kit according to claim 11 wherein said MHC-class I antigen is a Human Leucocyte Antigen (HLA)-ABC surface antigen and said ligand is an anti-HLA-ABC antibody.

13. A test kit according to claim 12 wherein said anti-HLA-ABC antibody is produced by the hybridoma PHM4.

* * * * *